US011523831B2

(12) United States Patent
Gorochow et al.

(10) Patent No.: US 11,523,831 B2
(45) Date of Patent: Dec. 13, 2022

(54) INTRASACCULAR FLOW DIVERTER

(71) Applicant: DePuy Synthes Products, Inc., Raynham, MA (US)

(72) Inventors: Lacey Gorochow, Miami, FL (US); Ariel Soto Del Valle, Hialeah, FL (US); Juan Lorenzo, Davie, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 211 days.

(21) Appl. No.: 16/863,334

(22) Filed: Apr. 30, 2020

(65) Prior Publication Data
US 2021/0338250 A1    Nov. 4, 2021

(51) Int. Cl.
*A61B 17/12*   (2006.01)
*A61M 25/00*  (2006.01)

(52) U.S. Cl.
CPC .. *A61B 17/12172* (2013.01); *A61B 17/12113* (2013.01); *A61M 25/0021* (2013.01); *A61B 2017/12054* (2013.01); *A61M 2025/0042* (2013.01)

(58) Field of Classification Search
CPC ........ A61B 17/12172; A61B 17/12113; A61B 2017/12054; A61M 25/0021; A61M 2025/0042
See application file for complete search history.

(56) References Cited

U.S. PATENT DOCUMENTS

| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |

(Continued)

FOREIGN PATENT DOCUMENTS

EP    3 607 895 A2    2/2020

OTHER PUBLICATIONS

EP Search Report dated Aug. 25, 2021 (9 pp.).
(Continued)

*Primary Examiner* — Katherine M Shi
*Assistant Examiner* — Mohammed S Adam
(74) *Attorney, Agent, or Firm* — Cohen & Hildebrand, PLLC

(57) ABSTRACT

Intrasaccular flow diverter including: an interior fill braid physically inverted over itself forming a proximal inverted end and an opposite free end; and a dome braid disposed distally of and secured to the interior fill braid. Subject to application of an external mechanical force, the dome braid is transitionable between an expanded state and a compressed state. The dome braid has a proximal end with an opening defined therein through which starting at the free end the interior fill braid is passable therethrough exerting a radially outward force on the dome braid. A delivery wire is releasably detachable from the proximal inverted end of the interior fill braid. The dome braid has a stiffer profile relative to that of the interior fill braid to maintain in position within the aneurysm the dome braid as the interior fill braid is advanced therein.

8 Claims, 5 Drawing Sheets

(56) References Cited

U.S. PATENT DOCUMENTS

| | | |
|---|---|---|
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0055515 A1* | 3/2018 | Greene, Jr. ...... A61B 17/12136 |
| 2018/0242979 A1 | 8/2018 | Lorenzo |
| 2020/0069313 A1 | 3/2020 | Xu et al. |

OTHER PUBLICATIONS

Woven EndoBridge (WEB) Aneurysm Embolization System—P170032 |FDA [online] Sequent Medical (later acquired by MicroVention), Jan. 28, 2019 [retrieved on Apr. 30, 2020]. Retrieved from the Internet:> URL: https://www.fda.gov/medical-devices/recently-approved-devices/woven-endobridge-web-aneurysm-embolization-system-p170032.

* cited by examiner

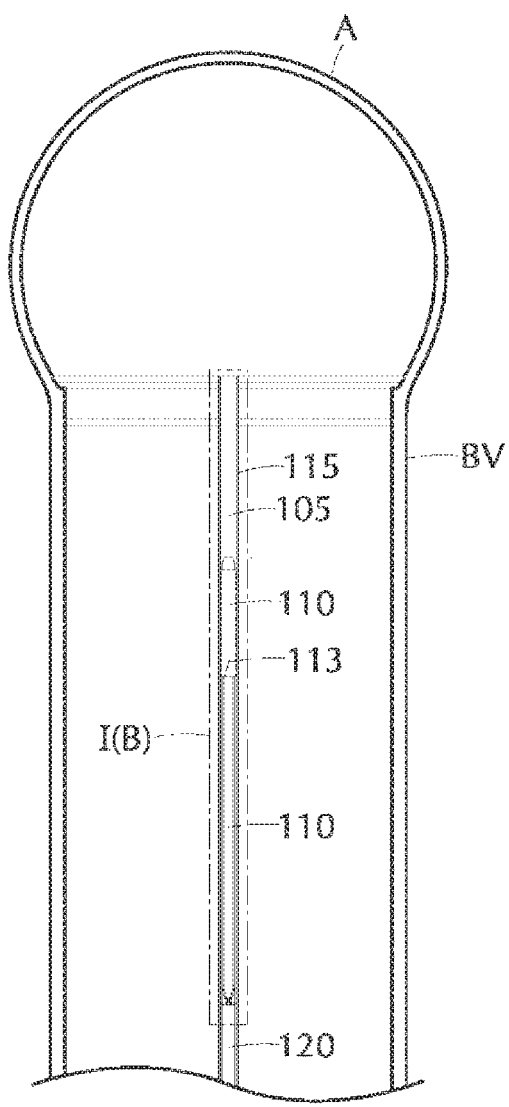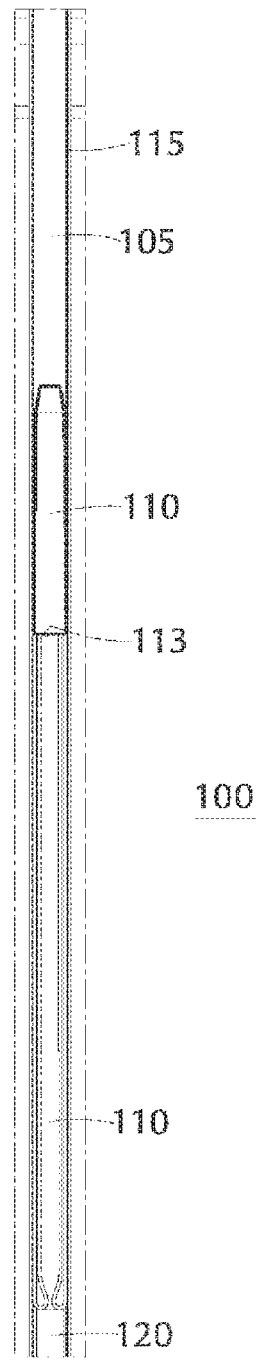
FIG. 1A
FIG. 1B

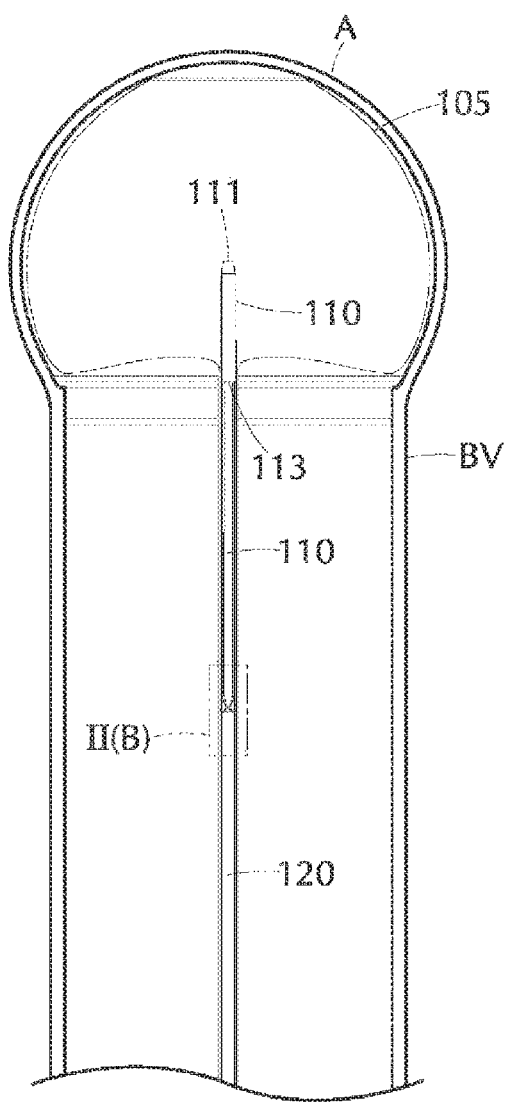 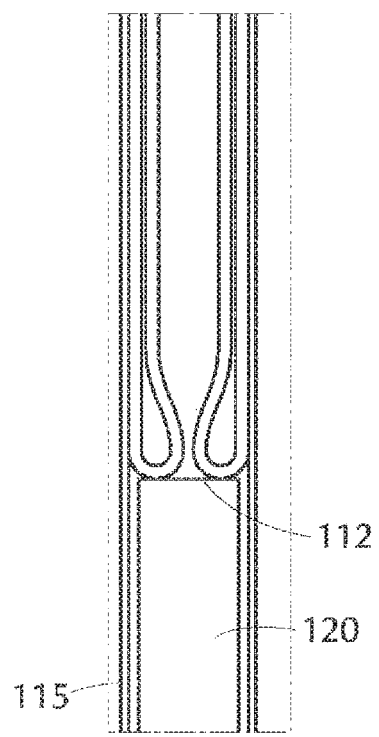
FIG. 2A
FIG. 2B

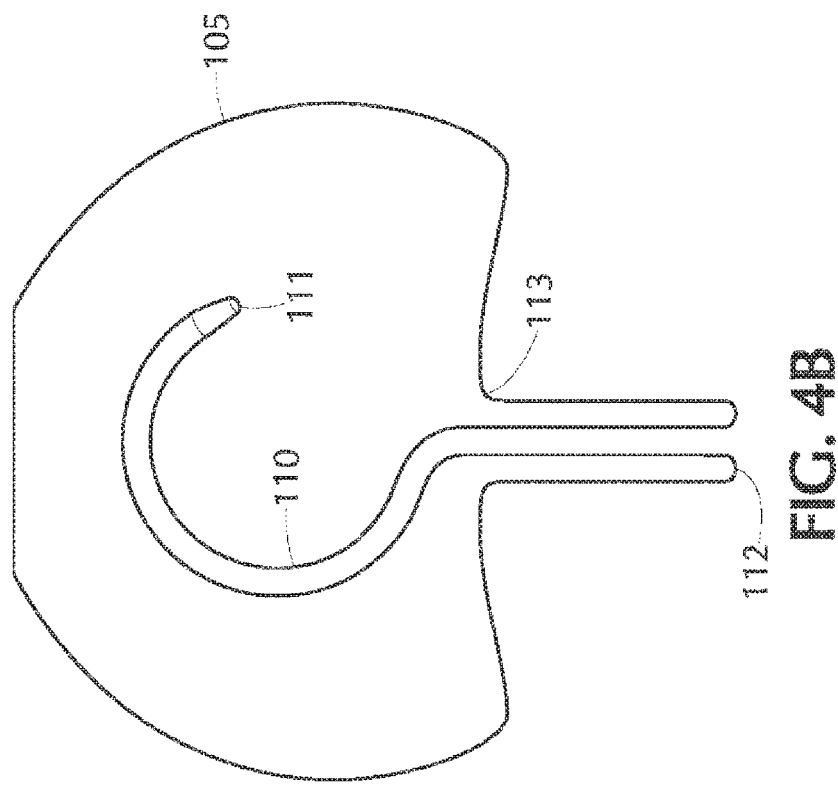
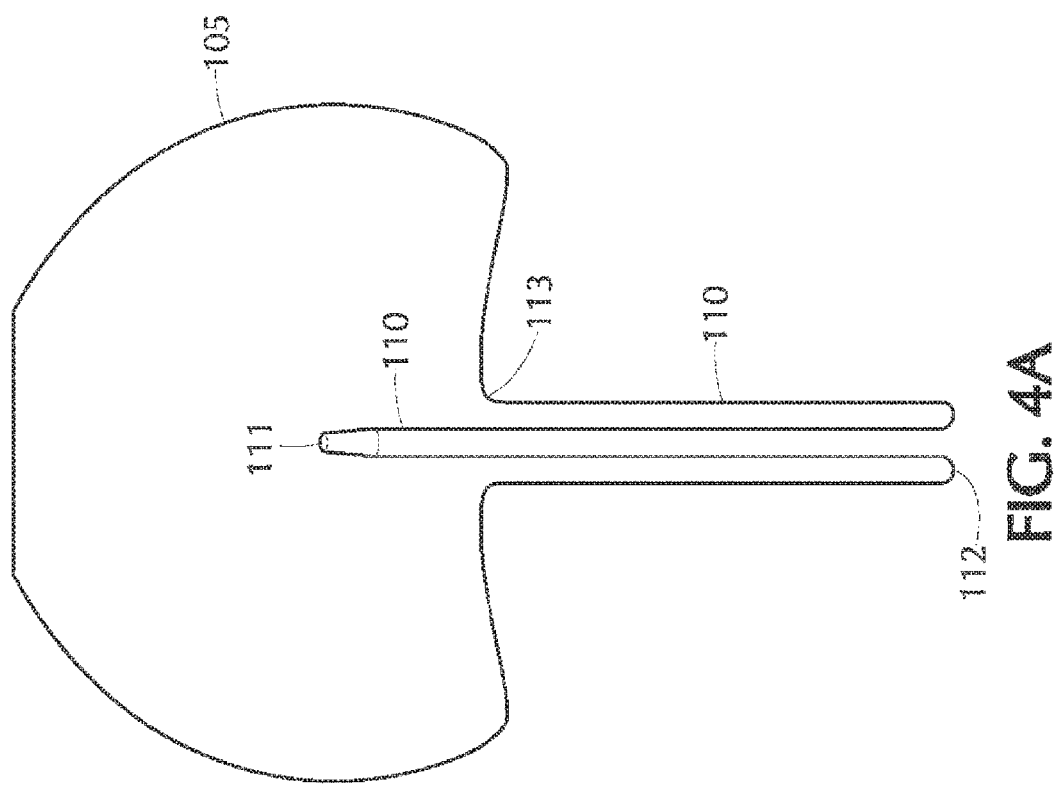

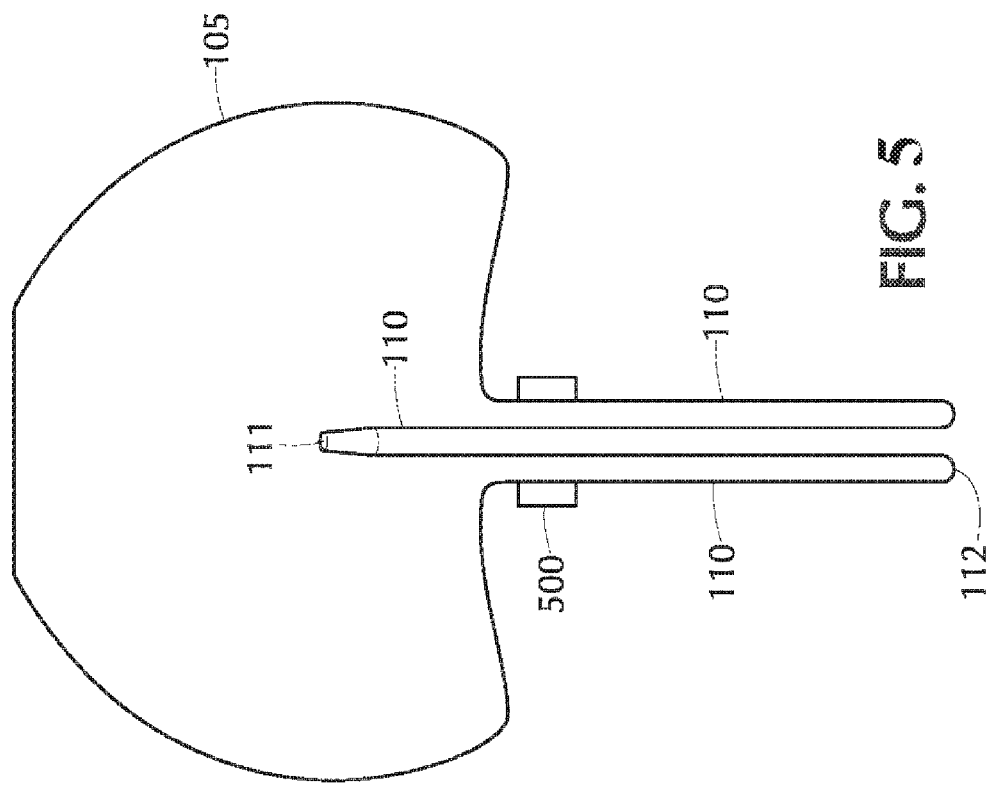
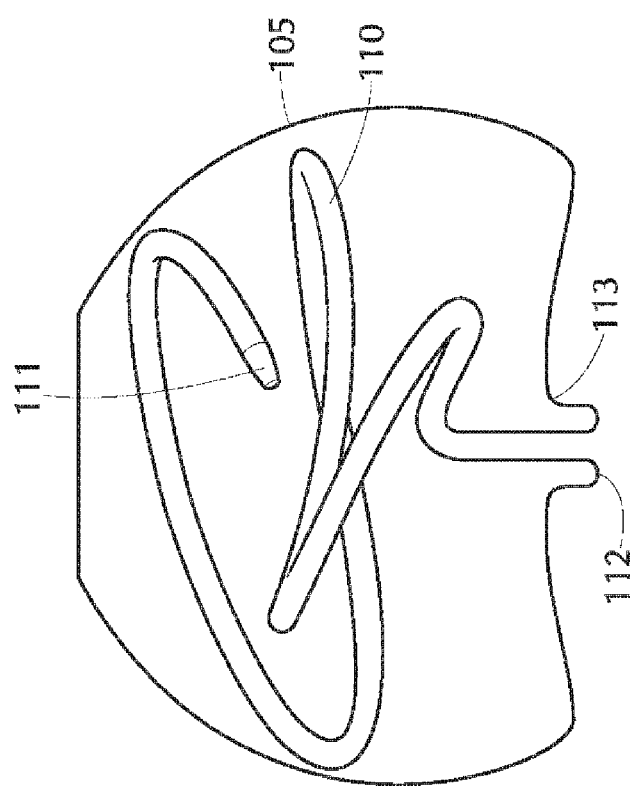

INTRASACCULAR FLOW DIVERTER

BACKGROUND OF THE INVENTION

Field of the Invention

The present invention relates to the endovascular treatment of intracranial aneurysms using an intrasaccular flow diverter and, in particular, to an improved intrasaccular flow diverter composed of two parts, namely, a dome braid and an interior fill braid advanceable therein.

Description of Related Art

Abnormal widening or dilation of the blood vessel walls is known as an aneurysm. Typically located in the heart (aortic) or brain (cerebral), such abnormalities in the vessel result in thinning, weakening and ballooning of the vessel wall making it prone to rupture and thus potentially resulting in death.

Aneurysms are generally treated by excluding the weakened part of the vessel from the arterial circulation. For treating a cerebral aneurysm, there are several forms of conventional treatment procedures including an invasive surgical procedure involving securing a clip around the neck of the aneurysm preventing blood from entering the aneurysm. A less invasive, non-surgical, treatment procedure fills or packs the aneurysm with vaso-occlusion devices (e.g., small, flexible wire coils) or embolic materials to induce thrombus and eventually clot off the aneurysm from blood flow in the vasculature. Conventional coils impose several drawbacks. One problem is that multiple coils (e.g., typically between 5-10 coils) are needed to pack the aneurysm, which requires additional time for implantation. Another recognized problem is that conventional coils have a tendency to shift in the aneurysm causing possible recanalization.

In lieu of conventional coils, intrasaccular flow diversion devices or disrupters (ISFD) may be implanted to divert or disrupt the flow of blood away from the aneurysm. One such device, the Woven EndoBridge (WEB device) Aneurysm Embolization System by MicroVention, Inc. is a braid shaped in a sphere. During implantation, the WEB device is introduced in the groin and delivered endovascularly to the intracranial aneurysm sac, where it deploys and fills the aneurysm. The mesh provides tension so that the device remains in place, disrupting blood flow to the aneurysm and thereby promoting thrombosis. Non-conformity of shapes between the non-spherical shaped aneurysm (e.g., elliptical, bilobular) and the braid shaped sphere of the flow diversion device may undesirably result in inadequate occlusion of the aneurysm.

It is therefore desirable to develop an improved intrasaccular flow diversion device (e.g., intrasaccular flow diverter) for the treatment of intracranial aneurysms that addresses the aforementioned problems associated with conventional treatment devices.

SUMMARY OF THE INVENTION

An aspect of the present invention is directed to an improved intrasaccular flow diversion device (e.g., intrasaccular flow diverter) for the treatment of intracranial aneurysms for filing, stabilizing and occluding the aneurysm using a single device.

Another aspect of the present invention is directed to an intrasaccular flow diverter including: an interior fill braid physically inverted over itself forming a proximal inverted end and an opposite free end; and a dome braid disposed distally of and secured to the interior fill braid. Subject to application of an external mechanical force, the dome braid is transitionable between an expanded state and a compressed state having a reduced overall diameter. The dome braid has a proximal end with an opening defined therein through which the free end of the interior fill braid is freely passable therethrough and into the dome braid. A delivery wire is releasably detachable from the proximal inverted end of the interior fill braid. The intrasaccular flow diverter is configured so that the dome braid has a stiffer profile relative to that of the interior fill braid to maintain in position within the aneurysm the dome braid as the interior fill braid is advanced therein.

Still another aspect of the present invention relates to a method for treatment of an aneurysm using the intrasaccular flow diverter as described in the preceding paragraph. A microcatheter is navigated through a vessel to a target site proximate the aneurysm. Using the delivery wire, the intrasaccular flow diverter is advanced through a lumen of the microcatheter while the dome braid and interior fill braid are each in the compressed state. Upon exiting from a distal end of the microcatheter, the dome braid is automatically deployed to the expanded state having an enlarged diameter filling the aneurysm, wherein only a distal portion of the interior fill braid including the free end is disposed interiorly of the deployed dome braid. Using the delivery wire, the intrasaccular flow diverter is further advanced through the lumen of the microcatheter until the inverted proximal end of the interior fill braid is positioned proximate to, but remains exterior of, the deployed dome braid. At that point, the delivery wire is released from the inverted proximal end of the interior fill braid allowing the interior fill braid to automatically transition to the expanded state interiorly exerting a force radially outward against the deployed dome braid to substantially conform in shape with that of the aneurysm.

A still further aspect of the present invention is directed to a method for treatment of an aneurysm using an intrasaccular flow diverter, wherein the intrasaccular flow diverter includes an interior fill braid and a dome braid disposed distally of the interior fill braid. First, the dome braid is deployed within the aneurysm to be treated; wherein the deployed dome braid reverts to a dome, sphere or hemispherical pre-formed shape. Thereafter, apposing so as to conform in shape the deployed dome braid to that of the aneurysm to be treated a radially outward force is imparted interiorly on the deployed dome braid using the interior fill braid introduced therein.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which:

FIG. 1A is an axial cross-sectional view of the present inventive intrasaccular flow diverter maneuvered through a lumen of a microcatheter to a target site in a vessel aligned with an aneurysm (A) to be treated;

FIG. 1B is an enlarged view of section I(B) of the present inventive intrasaccular flow diverter of FIG. 1A;

FIG. 2A is an axial cross-sectional view of the present inventive intrasaccular flow diverter wherein the dome braid is deployed in the aneurysm to be treated and a portion of the free end of the interior fill braid is emerging interiorly thereof;

FIG. 2B is an enlarged view of section II(B) of the intrasaccular flow diverter of FIG. 2A illustrating the inverted proximal end of the interior fill braid secured to the distal end of the pusher or deliver wire;

FIGS. 4A-4C represent enlarged partial views in sequence of the intrasaccular flow diverter illustrating the connection point or interface between the dome braid and the interior fill braid of FIG. 2A at three different stages of advancement in a distal direction of the interior fill braid through the microcatheter and into the cavity of the stationary deployed dome braid; wherein FIG. 4A is an enlarged partial view of the interior fill braid of the intrasaccular flow diverter of FIG. 2A wherein the free end of the interior fill braid is beginning to emerge into the deployed dome braid; FIG. 4B is an enlarged partial view of the interior fill braid extending further and partially deployed inside the deployed dome braid; while FIG. 4C is an enlarged partial view of the interior fill braid of the intrasaccular flow diverter of FIG. 3A wherein the interior fill braid extends even further and is fully deployed inside the deployed dome braid; and FIG. 5 is an enlarged partial view of the intrasaccular flow diverter of FIG. 2A depicting a particular embodiment in which securement between the neck of the deployed dome braid and the interior fill braid at the connection point or interface is accomplished using a crimped marker band.

DETAILED DESCRIPTION OF THE INVENTION

Figure 3A:
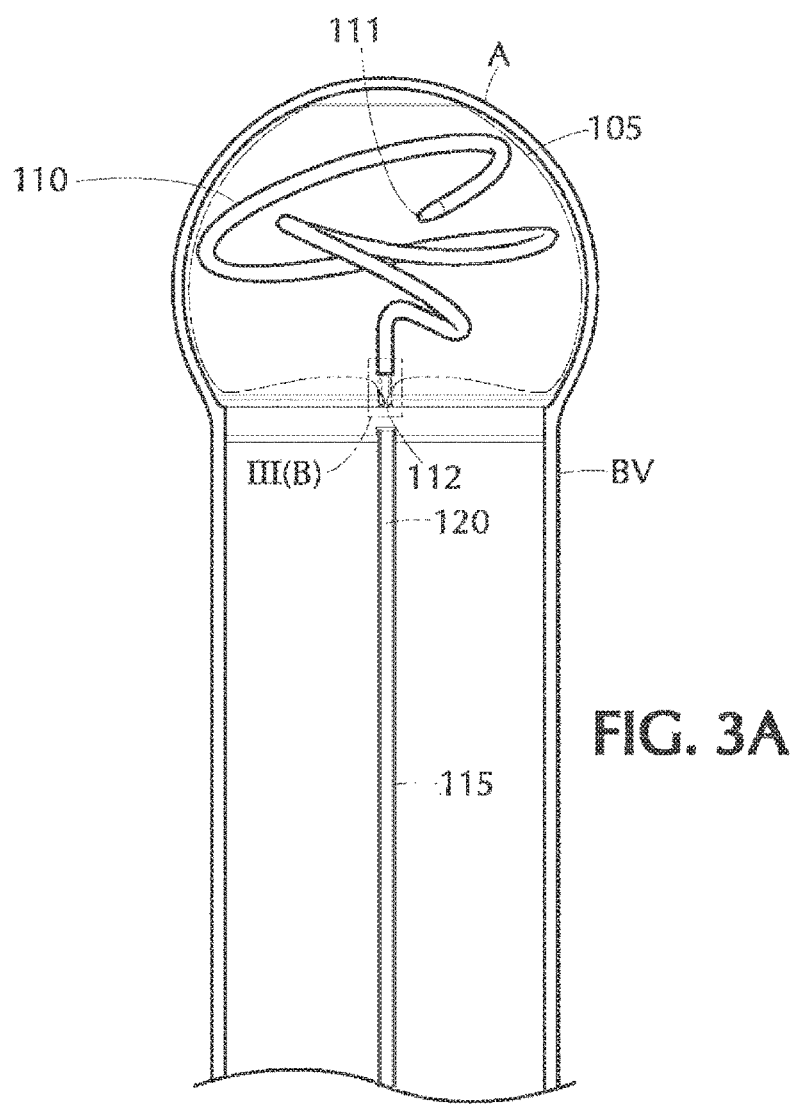
FIG. 3A is an axial cross-sectional view of the present inventive intrasaccular flow diverter device with the deployed interior fill braid disposed interiorly of the deployed dome braid apposing the aneurysm to be treated, after being released from the pusher or delivery wire.

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot" or "blockage" are used interchangeably.

FIG. 1A depicts the present inventive intrasaccular flow diverter 100 maneuvered through a blood vessel (BV) via a lumen of a microcatheter 115 to a target site aligned with an aneurysm (A) to be treated. While FIG. 1B, depicts an enlarged view of section I(B) of the intrasaccular flow diverter 100 in FIG. 1A. Referring to the enlarged view in FIG. 1B, intrasaccular flow diverter 100 is composed of two parts, that is, a dome braid 105 disposed distally of an interior fill braid 110 "socked in" within itself, as described in further detail below. Both the dome braid and interior fill braid 105, 110, respectively, are in a compressed state in FIGS. 1A & 1B. An open proximal end of the dome braid 105 is permanently, fixedly or non-releasably attached to an open distal end of the interior fill braid 110 at a connection point or interface 113. Various configurations are contemplated and within the intended scope of the present invention for connecting, attaching or securing the dome braid 105 to the interior fill braid 110 at the connection point or interface 113. In FIGS. 1A, 1B, 2A, 2B, 3A, 3B, 4A-4C the connection point or interface 113 between dome braid 105 and interior fill braid 110 is a laser weld. Other conventional non-mechanical forms of attachment such as, but not limited to adhesive is possible. Alternatively, a mechanical device such as a band or ring 500 crimped about the two braids 105, 110 may be used to physically secure the two components together, as depicted in FIG. 5. The band or ring is preferably: (i) made of a radiopaque material; (ii) includes one or more radiopaque features; or (iii) has at least a portion thereof with a radiopaque material covering layer to aid in visibility during maneuvering of the intrasaccular flow diverter through the vasculature to the target site using conventional imaging technology.

Addressing each component separately, dome braid 105 is a self-expanding braid, mesh, cage or skeleton with a plurality of openings defined therein. The dome braid is made of a biocompatible material for which the pattern, braid angle and number of wires comprising the braid may be selected, as desired. Upon application of an external physical mechanical force (e.g., during insertion into and advancement through the lumen of the microcatheter 115), dome braid 105 is collapsible to a compressed or contracted state having a cylindrical tube configuration sufficiently reduced in overall diameter to be receivable within the lumen of a microcatheter 115. Absent or free of application of an external physical mechanical force (e.g., prior to the dome braid being introduced into the lumen of the microcatheter; and thereafter upon the dome braid exiting from the distal end of the microcatheter), dome braid 105 is in an expanded or non-compressed state having a "domed", spherical or hemi-spherical shape with an enlarged or maximum overall diameter.

Interior fill braid 110 is similarly configured as a self-expanding braid, mesh, cage or skeleton with a plurality of openings defined therein. During insertion of the intrasaccular flow diverter device 100 into the lumen of the microcatheter, the interior fill braid 110 is in a contracted or compressed state taking on a substantially linear configuration thus reduced in overall diameter to be receivable within the lumen of the microcatheter 115. Free or absent of application of an externally applied physical mechanical force (e.g., prior to the interior fill braid being introduced in the lumen of the microcatheter; and thereafter upon the interior fill braid exiting from the distal end of the microcatheter), the interior fill braid 105 is in a non-compressed or expanded state having a complex helical, spiral or ribbon pre-formed configuration that fills and pushes radially outward from within the deployed dome braid 105.

Dome braid 105 is designed to have a profile stiffness greater relative to that of the interior fill braid 110. This increased profile stiffness of the dome braid may be achieved by varying one or more of the following properties: (i) increase the thickness (diameter) of the individual wires forming the braid, mesh, cage or skeleton; (ii) decrease the braid angle; and (iii) increase the number of wires forming the braid. In contrast, the reduced profile stiffness of the interior fill braid 110 is sufficiently flexible or pliable to allow the interior fill braid to be physically turned outside in (i.e., its outer surface turned inward like that of a sock or a sleeve). Hereinafter, the interior fill braid while in a state turned "outside in" is hereinafter generically referred to as being—inverted, retracted, drawn, flipped or socked—inward onto itself. That is, while the distal end of the interior fill braid 110 remains permanently secured, connected or attached to the open proximal end (neck) of the dome braid 105 at the connection point or interface 113, the opposite free end 111 of the interior fill braid 110 is "socked inwards" or "drawn inwards" in a distal direction through the axial passageway defined within the interior fill braid forming an inverted proximal end 112. In turn, the inverted proximal end 112 of the interior fill braid 110 is releasably/detachably secured, attached, connected or mounted to a pusher or delivery wire 120. Intrasaccular flow diverter 100 is advanceable in a distal direction through the lumen of the microcatheter 115 using the pusher or delivery wire 120. Preferably, the interior fill braid 110 is inverted, retracted, drawn, flipped or socked onto itself in a distal direction to such extent that the free inverted end of the interior fill braid extends beyond the connection point or interface 113 and into the dome braid 105. As a result of its increased profile stiffness deployed dome braid 105 maintains its shape while the inverted interior fill braid 110 is advanced in a distal direction into the cavity formed by the deployed dome braid 105.

During manufacture of the intrasaccular flow diverter (in a non-compressed or expanded state not subject to application of an external physical mechanical force), dome braid 105 is pre-formed to have a domed, spherical or hemispherical shape; whereas interior fill braid 110 has a complex spiral, helical or any other pre-formed shape sufficient to apply physical force radially outward against the interior wall of the deployed dome braid apposing the aneurysm.

As illustrated in FIG. 1A, during treatment of the aneurysm using the present inventive intrasaccular flow diverter 100, microcatheter 115 is initially introduced into the body, preferably via the groin, and maneuvered intravascularly through the blood vessel (BV) to a target site (e.g., substantially aligned with a target aneurysm (A) to be treated). While the dome braid 105 and interior fill braid 110 are both in a compressed or contracted state reduced in overall diameter (as shown in FIGS. 1A & 1B), the present inventive intrasaccular flow diverter 100 is advanced in a distal direction through the lumen of the microcatheter 115 using a pusher or delivery wire 120. In this compressed or contracted state dome braid 105 is collapsed while interior fill braid 110 is maintained in a substantially straight or linear configuration such that each component has a reduced overall diameter receivable within the lumen of the microcatheter.

As the intrasaccular flow diverter 100 is advanced distally through the microcatheter 115 using the pusher or delivery wire 120, braid dome 105 is first to emerge from the distal end of the microcatheter 115. Dome braid 105 is fully deployed when the connection point 113 is proximate the distal end of the microcatheter 115. No longer physically constrained by the interior walls of the microcatheter 115, braid dome 105 automatically reverts to its pre-formed spherical or hemispherical ("dome") shape (i.e., returning to its non-compressed state) having an enlarged or expanded overall diameter filling the aneurysm to be treated, as shown in FIG. 2A. Also visible in the illustration in FIG. 2A is that portion of the free end 111 of the interior fill braid 110 that extends in a distal direction beyond the connection point or interface 113 and into the cavity of the deployed dome braid 105. At this stage of treatment, since only a relatively small portion of the inverted fill braid 110 extends into the cavity of the deployed dome braid 105, despite not being constrained by the microcatheter 115, that exposed portion of the interior fill braid nevertheless remains substantially linear or straight.

As previously mentioned, since the dome braid 105 has a stiffer profile relative to that of the interior fill braid 110, the deployed dome braid 105 remains stationary in the aneurysm to be treated as the interior fill braid 110 is pushed or advanced further in a distal direction through the neck and into the cavity of the dome braid 105 using the pusher or delivery wire 120. With the continued advancement of the intrasaccular flow diverter in a distal direction, the increasing portion of the interior fill braid 110 that is no longer constrained by the microcatheter automatically reverts back to its complex helical or spiral pre-formed shape, as depicted in FIG. 4B.

Figure 3B:
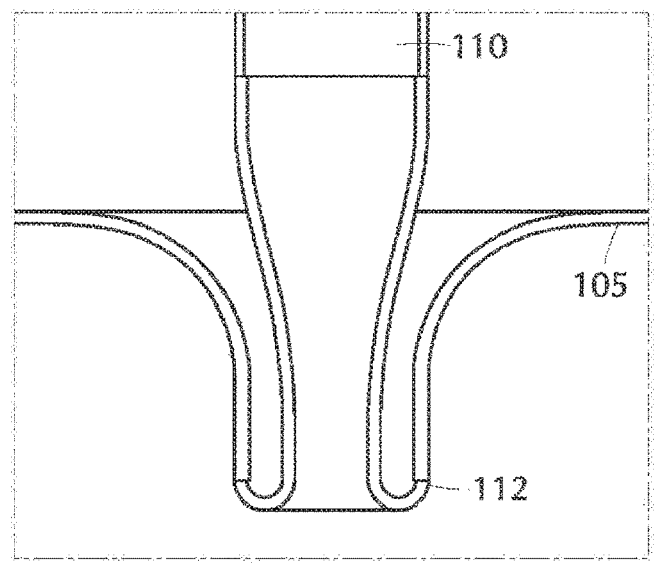
FIG. 3B is an enlarged view of section III(B) of the intrasaccular flow diverter in FIG. 3A illustrating the inverted proximal end of the interior fill braid free of the delivery or pusher wire.

In FIG. 3A, the interior fill braid 110 is still further advanced in a distal direction by the interventionalist using the pusher or delivery wire 120 through the neck and interiorly into the cavity of the expanded dome braid 105. Advancement of the interior fill braid 110 ceases when the inverted proximal end 112 of the interior fill braid 110 is exterior of and proximate the proximal opening (neck) of the deployed dome braid 105. At that point, the pusher or delivery wire 120 is released or detached from the proximal inverted end 112 of interior fill braid 110, whereupon the pusher or delivery wire 120 is withdrawn in a proximal direction through the microcatheter 115 from the body. FIG. 3B is an enlarged section III(B) in FIG. 3A of the inverted proximal end 112 of the interior fill braid 110 released from the pusher or delivery wire 120. Within the deployed dome braid 105 the detached interior fill braid 110 automatically deploys returning to its non-inverted (pre-shaped) state (e.g., a complex spiral shape, helical shape or any other desirable shape) applying a radially outward force on the interior wall of the deployed dome braid apposing the aneurysm, as depicted in FIG. 3A. Even when the interior fill braid 110 is fully deployed and free from the pusher or delivery wire 120 the inverted proximal end 112 of the interior fill braid 110 remains exterior of the deployed dome braid 105. Releasement or detachment of the pusher or delivery wire 120 from the proximal inverted end 112 of the interior fill braid 110 may be accomplished in any number of conventional ways. For example, release may occur automatically when a simple pusher or delivery wire exits from the distal end of the microcatheter. Alternative electrical, mechanical or hydraulic detachment processes or mechanisms are contemplated to achieve deployment.

The inverted interior fill braid of the present inventive intrasaccular flow diverter has been described above as being sufficiently flexible or pliable to permit the interior fill braid to be physically turned "outside in" (i.e., its outer surface turned inward like that of a sock or a sleeve). Such is the case where the distal end of the non-inverted interior fill braid is first connected, secured or attached to the proximal opening (neck) of the dome braid 105 at the connection point or interface 113 before the interior fill braid is inverted, retracted, socked or drawn onto itself. However, if the interior fill braid is initially inverted, retracted, socked or drawn onto itself prior to being connected to the proximal opening (neck) of the dome braid 105, it is contemplated that the interior fill braid may be inverted, retracted, socked or drawn onto itself either: by turning the "outside in", i.e., drawing the free end 111 inwards in a distal direction through the axial passageway defined within the interior fill braid forming the inverted proximal end 112; or turning the "inside out", i.e., drawing the free end 111 outwards in a distal direction over the outside of the interior fill braid forming the inverted proximal end 112. Regardless of the process followed to produce the inverted interior fill braid (irrespective of whether the interior braid is turned "outside in" or "inside out") the resulting structure is the same. That is, the inverted interior fill braid is non-releasably secured to the neck of the dome braid at the connection point 113, has a free end 111 disposed inside the cavity of the dome braid 105, and an inverted proximal end 112. Thus, to encompass either process the term "inverted" is generically defined as drawn back over itself, encompassing both "drawn inward"/ "outside in" or "drawn outward"/inside out".

The present inventive intrasaccular flow diverter provides numerous advantages some of which are summarized herein. On the one hand, the expanded dome braid 105 retains interiorly therein the deployed interior fill braid 110 restricting shifting or movement of the interior fill braid, while simultaneously the deployed interior fill braid 110 apposing the aneurysm results in the deployed dome braid substantially conforming in shape to that of the aneurysm. Accordingly, the present inventive intrasaccular flow diverter may universally be used for treatment of a wide variety of shape and size aneurysms with improved adequacy of occlusion. In addition, the neck of the deployed dome braid seals the aneurysm. The multicomponent structure of the present inventive intrasaccular flow diverter both fills the aneurysm with the deployed dome braid while simultaneously occluding the aneurysm with the deployed interior fill braid exerting force radially outward from within. Moreover, the present inventive intrasaccular flow diverter fills and occludes the aneurysm using a single device, which heretofore required packing of a plurality (e.g., 5-10) of coils requiring more time during treatment and risk of shifting.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An intrasaccular flow diverter comprising:
    an interior fill braid physically inverted over itself forming a proximal inverted end and an opposite free end;
    a dome braid disposed distally of and secured to the interior fill braid; subject to application of an external mechanical force, the dome braid being transitionable between an expanded state and a compressed state having a reduced overall diameter; the dome braid having a proximal end with an opening defined therein through which the free end of the interior fill braid is freely passable therethrough and into the dome braid; and
    a delivery wire releasably detachable from the proximal inverted end of the interior fill braid;
    wherein the dome braid has a stiffer profile relative to that of the interior fill braid.

2. The intrasaccular flow diverter according to claim 1, wherein: (i) the interior fill braid has a complex spiral or helical pre-formed shape in the expanded state; and a substantially linear configuration in the compressed state; and (ii) the dome braid has a domed, spherical or hemi-spherical pre-formed shape in the expanded state; and a cylindrical tube configuration in the compressed state.

3. The intrasaccular flow diverter according to claim 1, wherein the dome braid and interior fill braid are secured together proximate the opening by a band marker.

4. The intrasaccular flow diverter according to claim 1, wherein the stiffer profile of the dome braid relative to that of the interior fill braid is achievable by of the following characteristics: (i) increase thickness of individual wires forming the dome braid; (ii) decrease braid angle between wires forming the dome braid; and/or (iii) increase number of wires forming the dome braid.

5. A method for treatment of an aneurysm using an intrasaccular flow diverter, wherein the intrasaccular flow diverter includes an interior fill braid physically invertible over itself forming a proximal inverted end and an opposite free end; a dome braid disposed distally of and secured to the interior fill braid; the dome braid being transitionable subject to application of an external mechanical force from an expanded state to a compressed state having a reduced overall diameter; the dome braid having a proximal end with an opening defined therein through which the free end of the interior fill braid is freely passable therethrough and into the dome braid; and a delivery wire releasably detachable from the proximal inverted end of the interior fill braid; wherein the dome braid has a stiffer profile relative to that of the interior fill braid; the method comprising the steps of:
    navigating a microcatheter through a vessel to a target site proximate the aneurysm;
    using the delivery wire, advancing the intrasaccular flow diverter through a lumen of the microcatheter while the dome braid and interior fill braid are each in the compressed state;
    upon exiting from a distal end of the microcatheter, automatically deploying the dome braid to the expanded state having an enlarged diameter filling the aneurysm, wherein only a distal portion of the interior fill braid including the free end is disposed interiorly of the deployed dome braid;
    while the deployed dome braid is maintained filling in the aneurysm, using the delivery wire to further advance the intrasaccular flow diverter through the lumen of the microcatheter until the inverted proximal end of the interior fill braid is positioned proximate to, but remains exterior of, the deployed dome braid; and
    releasing the delivery wire from the inverted proximal end of the interior fill braid allowing the interior fill braid to automatically transition to the expanded state, interiorly exerting a force radially outward against the deployed dome braid to substantially conform in shape with that of the aneurysm.

6. The method according to claim 5, wherein: (i) the interior fill braid has a complex spiral or helical pre-formed shape in the expanded state; and a substantially linear configuration in the compressed state; and (ii) the dome braid has a domed, spherical or hemi-spherical pre-formed shape in the expanded state; and a cylindrical tube configuration in the compressed state.

7. The method according to claim 5, wherein the dome braid and interior fill braid are secured together proximate the opening by a band marker.

8. The method according to claim 5, wherein the stiffer profile of the dome braid relative to that of the interior fill braid is achieved by of the following characteristics: (i)

increase thickness of individual wires forming the dome braid; (ii) decrease braid angle between wires forming the dome braid; and/or (iii) increase number of wires forming the dome braid.

* * * * *

UNITED STATES PATENT AND TRADEMARK OFFICE
CERTIFICATE OF CORRECTION

| | | |
|---|---|---|
| PATENT NO. | : 11,523,831 B2 | Page 1 of 1 |
| APPLICATION NO. | : 16/863334 | |
| DATED | : December 13, 2022 | |
| INVENTOR(S) | : Gorochow et al. | |

It is certified that error appears in the above-identified patent and that said Letters Patent is hereby corrected as shown below:

In the Claims

Column 8, Claim 4, Line 3, delete "of" (second occurrence).

Column 8, Claim 5, Line 36, after "," insert --and--.

Column 8, Claim 8, Line 3, delete "of".

Signed and Sealed this
Twenty-first Day of March, 2023

Katherine Kelly Vidal
*Director of the United States Patent and Trademark Office*